United States Patent [19]

Tiger

[11] 4,161,180

[45] Jul. 17, 1979

[54] SUNTRAP SOLAR RADIATION COLLECTOR

[76] Inventor: Howard L. Tiger, Eagle Ridge Way, West Orange, N.J. 07052

[21] Appl. No.: 810,400

[22] Filed: Jun. 27, 1977

[51] Int. Cl.$^2$ ............................................. A61H 33/06
[52] U.S. Cl. ................................................. 128/372
[58] Field of Search ............... 128/372, 270, 293, 362; 135/1 R

[56] References Cited

U.S. PATENT DOCUMENTS

| | | | |
|---|---|---|---|
| 2,478,765 | 8/1949 | Kim | 128/270 |
| 2,834,351 | 5/1958 | Garson | 128/372 |
| 3,461,878 | 8/1969 | Southard | 128/372 |
| 3,625,434 | 12/1971 | Kitover | 128/372 |

FOREIGN PATENT DOCUMENTS

| | | | |
|---|---|---|---|
| 591175 | 4/1925 | France | 128/372 |
| 224311 | 2/1943 | Switzerland | 128/372 |

*Primary Examiner*—Lawrence W. Trapp

[57] ABSTRACT

A portable and adjustable device such as a chair is provided with upper and lower body-enveloping members for wind protection and control of exposure to solar radiation. A foot support is provided for sustaining the weight of the feet and legs. The device is preferably in the form of a rocking-chair or the like with retaining means to hold it at a desired angle of tilt, and may have a safety stop to prevent the user from tilting too far back and falling. An indicator may also be provided, to assist in determining the optimum azimuthal orientation and degree of tilt for maximizing the effective reception of solar radiation.

11 Claims, 3 Drawing Figures

4,161,180

SUNTRAP SOLAR RADIATION COLLECTOR

BACKGROUND OF THE INVENTION

The beneficial effects, both therapeutic and cosmetic, of exposure of the body to sunlight are too well known to require elaboration.

Attempts to avail oneself of these beneficial effects, however, are frequently beset by difficulties, chief among which is the chilling effect of wind. Even on bright sunny days, when the air is warm, e.g. from passage over extensive areas of sun-heated land, the effect of wind may exert a chilling effect by hastening the rate of evaporation of perspiration, and by stirring up airborne dust and debris. On days when the sunlight is relatively weak, whether because of intervening clouds or haze or because of the angle of incidence of the sun's rays upon the surface of the earth (particularly during the cooler fall, winter and spring months), its warming effect is appreciably diminished, and even a slight movement of air may create a distinctly uncomfortable chill.

In order to illustrate the importance of effective collection of radiation to comfort, a series of readings were taken at various intervals on opposite sides, separated by about 35 feet, of the same building (i.e. the inventor's residence). The two sides selected were the shady (northwesterly) and the sunny (easterly—southeasterly) sides. The times of the readings, and the values observed, are set forth in the following Table:

| Date | Time | Temp. °F. NW | SE |
|---|---|---|---|
| 2/27/74 | 1 PM | 30 | 72 |
| 3/14/74 | 2 PM | 38 | 82 |
| 4/7/74 | 1:30 PM | 50 | 93 |
| 5/7/74 | 2 PM | 49 | 81 (95° F. on dark wool coat; better wind shelter and orientation) |
| 5/8/74 | Noon | 54 | 100 |
| 7/8/74 | Noon to 1:30 PM | 79 | 111 (117 w/darker background and 120 w/15° rotation towards W) |
| 1/15/77 | Noon | 26 | 80 |
| 2/1/77 | 1 PM | 19 | 56 (some wind) |

Numerous expedients have been employed to permit exposure to solar radiation while ameliorating the cooling effect of air movement. Among these may be mentioned, for example, such devices as cabana chairs, beach umbrellas and the like (which may also be used for the opposite purpose, i.e. to protect the user from excessively intense or prolonged radiation), and plastic canopies or screens designed to shield the user from the wind, while allowing free access of radiation, or at least to that portion of the radiation to which the shield is transparent.

These expedients, while successful to a degree, cannot be completely effective because of the nature of air currents. When an air current encounters an obstacle of the type just described, it does not ordinarily split and pass around the obstacle in laminar flow fashion, at least unless the obstacle is aerodynamically engineered and properly oriented to achieve such laminar flow. Rather, it tends to create a partial vacuum on the side opposite to that against which the air current collides, and draws air in from the sides in swirling eddy currents, which are nearly as desirable as the primary air current from the viewpoint of comfort.

OBJECTS OF THE INVENTION

An object of this invention, therefore, is to provide an improved apparatus for collecting solar radiation and exposing the body of the user thereto.

Another object is to provide an improved apparatus for exposing the body to solar radiation, while protecting it from the effects of air movement.

Still another object is to provide such an apparatus, wherein the object of protecting the body of the user from a primary air current is not wholly nor partially defeated by the generation of secondary air currents in the form of turbulence around the boundaries of a shield.

Other objects, features and advantages will become apparent from the following more complete description and claims, taken together with the accompanying drawings.

BRIEF STATEMENT OF THE INVENTION

The above and other objects are accomplished according to the present invention which, in one particularly desirable aspect contemplates:

a suntrap for simultaneously exposing the user to the rays of the sun and shielding said user from the wind, comprising in combination:

body support means for sustaining the weight of the user's body upwardly of the knees;

foot support means for sustaining the weight of said user's legs and feet;

upper enveloping means for enclosing said user's body substantially completely from the knee area to and including the head;

said upper enveloping means being provided with means for admitting the rays of the sun so as to impinge directly upon said user's body, and lower enveloping means adapted to enclose said user's feet and legs to approximately the knee area;

said lower enveloping means cooperating with said upper enveloping means to encase the user's entire body in loose fashion, while providing sufficient communication with the ambient air to ensure an adequate supply of air for breathing.

BRIEF DESCRIPTION OF DRAWINGS

In the accompanying drawings, in which the same reference numerals are used to designate the same elements throughout.

DESCRIPTION OF PREFERRED EMBODIMENTS

Figure 3:
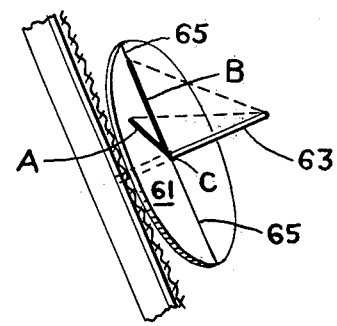
FIG. 3 is a detail perspective of one feature.
Figure 1:
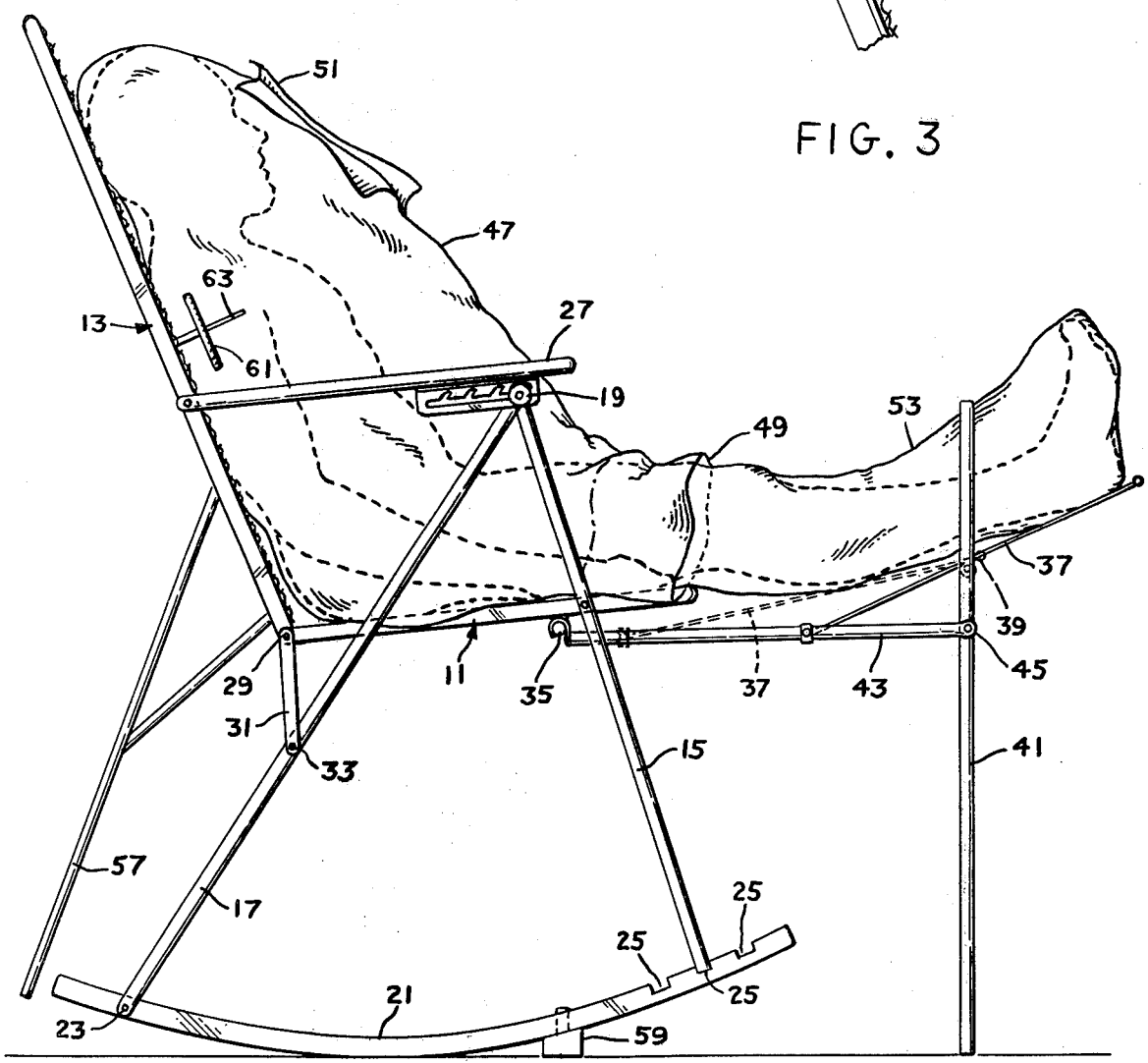
FIG. 1 is a side elevation of an apparatus according to a preferred embodiment of the invention, in the form of a rocking chair.

Referring to the drawings, the apparatus of this invention as there illustrated comprises body support means in the form of a seat 11 and a backrest 13 which extends upwardly sufficiently for it to function also as a headrest. The body support means is supported in conventional manner by forwardly-extending legs 15 and rearwardly-extending legs 17. Legs 15 and 17 are pivotally connected on each side, as indicated at 19. Legs 15 and 17 in turn are connected to rockers 21, legs 17 by pivotal connections as indicated at 23, and legs 15 by fitting into notches 25 provided for the purpose in the tops of rockers 21.

Arm-rests 27 are provided, and are pivotally connected at their rearward ends to backrest 13 and at or near their forward ends to the upper ends of legs 15.

Figure 2:
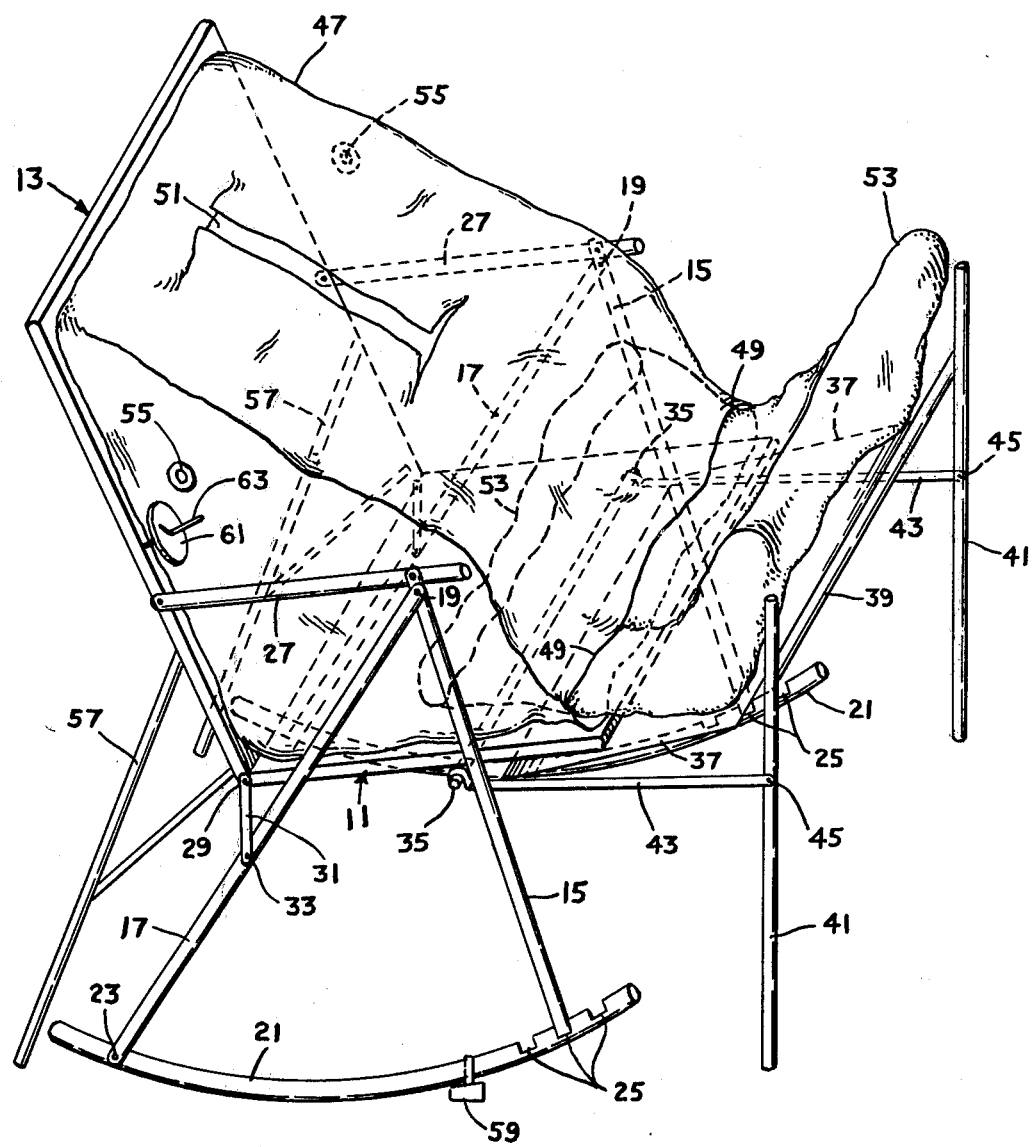
FIG. 2 is a perspective view of the apparatus according to FIG. 1, showing certain additional details of construction.

Seat 11 is pivotally connected to backrest 13, and also to supporting links 31, as indicated at 29. Supporting links 31, in turn, are pivotally connected to legs 17, as indicated at 33. Seat 11 further supports at an appropriate point between pivotal connection 29 and the forward edge of seat 11, a horizontal transverse support bar 35, which extends the width of the seat 11 as shown in FIG. 2. A safety brace 57 is preferably connected to backrest 13, in position to bear against the ground or other supporting surface, so as to eliminate the possibility of the user rocking back too far and falling.

From the foregoing description, taken with the drawing, it will be appreciated that the above mentioned members define a collapsible folding rocking chair, wherein the angle between seat 11 and backrest 13, when in open or operative position, may be varied for comfort or for maximum absorption of solar radiant energy, by inserting the lower ends of legs 15 into various of the notches 25. Also, the angle of tilt of the apparatus as a whole may be adjusted and maintained by the use of adjustable wedges or chocks 59 adjustably attached to rockers 21.

The supporting structure of the apparatus also comprises a separate, foldable and demountable foot support 37 in the form of a planar member supported at its distal or foot-supporting end by a horizontal transverse bar 39 secured at an adjustable height to vertical support members 41, and at its proximal end by horizontal support members 43 which in turn rests at one end on horizontal transverse support bar 35 and is pivotally secured at its other end to vertical support member 41, as indicated at 45. It will be noted that the angle with the horizontal of foot support 37 may be adjusted by adjusting the height of bar 39, and that the whole foot-supporting assembly can be demounted by removing foot support 37, disengaging horizontal support members 43 from horizontal transverse support bar 35, and folding horizontal support member 43 down to vertical support member 41 about pivot 45.

An upper enveloping means is provided in the form of a plastic bag 47 adapted to enclose the body of the user of the apparatus, from the head down to approximately the knee area and terminating in a lower margin 49. The entire bag 47 is preferably made of transparent plastic, although if desired, the back and sides thereof may be made of opaque, preferably black material, to absorb radiant energy which bypasses the body of the user. This absorbed radiant energy will further warm the interior of the bag by conduction to the internal atmosphere.

The front of the bag may be provided with openable panels 51, so as to permit direct access to solar radiation when that is desired.

A lower enveloping means is provided in the form of plastic bag 53, adapted to contain loosely the feet and legs of the wearer, to or somewhat beyond the lower margin 49 of the plastic bag 47 constituting the upper enveloping means. The two plastic bags 47 and 53 may be loosely joined in overlapping relation as shown, in which case an adequate air supply for breathing will be provided at the loose junction. Alternatively, the upper and lower bags may be tightly joined, as by a slide fastener or the like (not shown), in which case it is desirable to provide open ports (FIG. 2) 55, independent of openable panels 51, in bag 47, to ensure an adequate supply of air for breathing.

The apparatus is preferably also provided with an orientation indicator consisting of a planar shadow-receiving member 61 attached to the backrest and in a plane parallel with said backrest, and a shadow-casting member 63 projecting outwardly from said shadow-receiving member in a direction normal thereto. The shadow-receiving member 61 has inscribed thereon an index line 65 extending vertically upward from the base of shadow-casting member 63. The use of the orientation indicator, referring particularly to FIG. 3, is as follows:

When the chair is initially positioned, the shadow cast by the shadow-casting member will generally fail to coincide with the index line, as illustrated at A. Failure to so coincide indicates that the backrest is turned to the left or right, rather than directly facing the incoming rays of the sun. The entire chair is then turned to the right or left, as required, to cause the shadow cast by shadow-casting member 63 to coincide with the index line 65, as illustrated at B. The backrest now faces the sun directly, in the horizontal plane; in the vertical plane, the backrest will ordinarily be found not to face directly the incoming rays of the sun, by reason of its tilt, and the amount of the discrepancy is proportional to the length of the shadow. The backrest is now tilted forward or back either relative to the remainder of the chair assembly or, alternatively, the entire chair may be rocked forward or back, until the shadow cast by shadow-casting member 63 is shortened to the vanishing point, as indicated at C. In these circumstances, the shadow point C will, on reaching its shortest length shift from one side of the shadow-casting member 63 to the other side of the member in response to motion of the chair. When this condition is achieved, the shadow-casting member 63 points directly at the sun, and the shadow-receiving member 61, the backrest, and the body of a person sitting in the chair are all in position to receive the most direct possible impingement of the sun's rays. Naturally, the apparent position of the sun is constantly changing, and a single setting of the chair with reference to the orientation indicator remains mathematically exact only for an instant. However, a single such setting is valid, for practical purposes, over an appreciable period of time before readjustment becomes necessary. In case the user desires to rest in the chair for an appreciable time, it may be desirable to compensate for the horizontal change in the apparent position of the sun (about 15° per hour) by setting the shadow line in advance of the index line by an amount equivalent to about half the expected change in the apparent horizontal position of the sun during the resting period, so that the optimum orientation will occur about halfway through the resting period. The chair, moreover, can be rotated to follow the sun by means of a turntable mounting, securing a rolling contact bearing under one of the rockers 21, and the like.

Compensation for changes in the apparent vertical elevation of the sun may be accomplished without leaving the chair by adjusting the angle of tilt of the chair back by slight modifications of a backrest tilting mechanism well known in patio chairs, indicated generally at 67.

While this invention has been described in terms of certain preferred embodiments and illustrated by a drawing, these are illustrative only, as many alternatives and equivalents will readily occur to those skilled in the art, without departing from the spirit and proper scope of the invention. The invention is therefore not to be construed as limited, except as set forth in the appended claims.

I claim:

1. A suntrap for exposing simultaneously the user to rays of the sun and shielding said user from wind, the suntrap comprising in combination:
   body supporting means for sustaining weight of the user's body upwardly of his knees;
   foot support means for sustaining the weight of said user's legs and feet;
   upper enveloping means for enclosing said user's body substantially completely from his knee area to and including his head;
   said upper enveloping means being provided with means for admitting the rays of the sun so as to impinge directly upon said user's body;
   lower enveloping means adapted to enclose said user's feet and legs to approximately the knee area;
   said lower enveloping means cooperating with said upper enveloping means to encase the user's entire body in loose fashion, while providing sufficient communication with ambient air to ensure an adequate supply of air for breathing;
   said body support being in the form of a chair; and
   said chair is a rocking chair with chocks and safety stops.

2. An apparatus according to claim 1, in which said chair is a foldable chair.

3. An apparatus according to claim 1, wherein said foot support is a planar member of adjustable horizontal angle and elevation, supported at its proximal end by a horizontal member projecting forwardly from said chair and at its distal end by a vertical member linked perpendicularly to said horizontal member.

4. An apparatus according to claim 1, wherein said means for admitting the rays of the sun comprises an openable panel in said upper enveloping means.

5. An apparatus according to claim 1, wherein said means for admitting the rays of the sun comprises a portion of said upper enveloping member which is transparent to the desired radiation.

6. Apparatus according to claim 1, wherein said communication with the ambient air is by way of a loose connection between said upper and said lower enveloping means.

7. Apparatus according to claim 1, wherein said communication with the ambient air is by way of open ports in at least one of said enveloping means.

8. Apparatus according to claim 1, further comprising means for obtaining optimal orientation of said body support means relative to the direction of the sun's rays.

9. (Second Amendment) Apparatus according to claim 8, wherein said means for obtaining optimal orientation comprises a planar, shadow-receiving surface parallel to the base of said body-support means and a shadow-casting means perpendicular to said shadow-receiving means, said shadow-casting and shadow-receiving means cooperating to indiciate optimum azimuthal orientation and optimum tilt of back-support means constituting a portion of said body-support means.

10. A suntrap for simultaneously exposing the user to the rays of the sun and shielding said user from the wind, comprising in combination:
    body support means for sustaining the weight of the user's body;
    upper enveloping means for enclosing said user's body substantially completely from the knee area to and including the head;
    said upper enveloping means being provided with means for admitting the rays of the sun so as to impinge directly upon the user's body;
    lower enveloping means adapted to enclose said user's feet and legs to approximately the knee area;
    said lower enveloping means cooperating with said upper enveloping means to encase the user's entire body in loose fashion, while providing sufficient communication with the ambient air to ensure an adequate supply of air for breathing;
    said body support means being in the form of a chair; and means for obtaining optimal orientation of said body support means relative to the direction of the sun's rays.

11. Apparatus according to claim 10, wherein said means for obtaining optimal orientation comprises a planar, shadow-receiving surface parallel to the base of said body-support means and a shadow-casting means perpendicular to said shadow-receiving means, said shadow-casting and shadow receiving means cooperating to indicate optimum azimuthal orientation and optimum tilt of back-support means constituting a portion of said body-support means.

* * * * *